(12) United States Patent
Saoji (10) Patent No.: US 9,227,060 B2
(45) Date of Patent: Jan. 5, 2016

(54) SYSTEMS AND METHODS OF FACILITATING MANUAL ADJUSTMENT OF ONE OR MORE COCHLEAR IMPLANT SYSTEM CONTROL PARAMETERS

(71) Applicant: Advanced Bionics AG, Staefa (CH)

(72) Inventor: Aniket Saoji, Newhall, CA (US)

(73) Assignee: Advanced Bionics AG, Staefa (CH)

( * ) Notice: Subject to any disclaimer, the term of this patent is extended or adjusted under 35 U.S.C. 154(b) by 0 days.

(21) Appl. No.: 14/160,929

(22) Filed: Jan. 22, 2014

(65) Prior Publication Data

US 2014/0135872 A1 May 15, 2014

Related U.S. Application Data

(62) Division of application No. 12/695,743, filed on Jan. 28, 2010, now Pat. No. 8,660,657.

(60) Provisional application No. 61/148,762, filed on Jan. 30, 2009.

(51) Int. Cl.
*A61N 1/36* (2006.01)
*A61N 1/372* (2006.01)
*A61N 1/05* (2006.01)

(52) U.S. Cl.
CPC ........ *A61N 1/36032* (2013.01); *A61N 1/37247* (2013.01); *A61N 1/0541* (2013.01); *A61N 1/37264* (2013.01)

(58) Field of Classification Search
CPC .......................... A61N 1/36032; H04R 25/606
USPC ..................................................... 607/57, 59
See application file for complete search history.

(56) References Cited

U.S. PATENT DOCUMENTS

| 6,205,360 | B1 | 3/2001 | Carter et al. |
| 6,862,359 | B2 | 3/2005 | Nordqvist et al. |
| 2004/0260362 | A1 | 12/2004 | Darley |
| 2005/0129262 | A1* | 6/2005 | Dillon et al. .................. 381/312 |
| 2006/0210103 | A1 | 9/2006 | Van den Heuvel |

OTHER PUBLICATIONS

International Search Report and Written Opinion received in International Application No. PCT/US2011/022205 dated Mar. 21, 2011.
Non-Final Office Action received in U.S. Appl. No. 12/695,743 dated Nov. 28, 2012.
Extended European Search Report received in European Patent Application No. 11737480.1 dated Jun. 6, 2013.

* cited by examiner

*Primary Examiner* — Alyssa M Alter

(74) *Attorney, Agent, or Firm* — ALG Intellectual Property, LLC (57) ABSTRACT

An exemplary system includes a sound processing unit configured to apply noise reduction to an audio signal in accordance with a noise reduction parameter, an implantable cochlear stimulator communicatively coupled to the sound processing unit and configured to apply stimulation representative of the noise reduced audio signal to a patient via one or more electrodes, and a user input facility communicatively coupled to the sound processing unit and that facilitates manual adjustment of the noise reduction parameter.

19 Claims, 11 Drawing Sheets

SYSTEMS AND METHODS OF FACILITATING MANUAL ADJUSTMENT OF ONE OR MORE COCHLEAR IMPLANT SYSTEM CONTROL PARAMETERS

RELATED APPLICATIONS

The present application is a divisional application of U.S. patent application Ser. No. 12/695,743, filed Jan. 28, 2010, which claims priority under 35 U.S.C. §119(e) to U.S. Provisional Patent Application No. 61/148,762, filed Jan. 30, 2009. The contents of both applications are hereby incorporated by reference in their entirety.

BACKGROUND INFORMATION

The sense of hearing in human beings involves the use of hair cells in the cochlea that convert or transduce audio signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that audio signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce audio signals into auditory nerve impulses. People who suffer from sensorineural hearing loss are unable to derive any benefit from conventional hearing aid systems.

To overcome sensorineural hearing loss, numerous cochlear implant systems—or cochlear prosthesis—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, an array of electrodes may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to auditory nerves within the cochlea via one or more of the electrodes.

When a cochlear implant system is initially implanted in a patient, it is usually necessary to fit the cochlear implant system to the patient. Such "fitting" includes adjustment of a variety of control parameters governing the operation of the cochlear implant system to values that are most effective and comfortable for the patient. However, it is often difficult or impossible to determine optimal values for many control parameters because they depend on the particular listening environment in which the patient is located. For example, optimal noise reduction parameters may be different in a noisy listening environment than in a quiet environment.

SUMMARY

An exemplary cochlear system includes a sound processing unit configured to process an audio signal, an implantable cochlear stimulator communicatively coupled to the sound processing unit and configured to apply stimulation representative of the audio signal to a patient via one or more electrodes in accordance with the processing of the audio signal, and a user input facility communicatively coupled to the sound processing unit. The sound processing unit and the implantable cochlear stimulator are configured to operate in accordance with a plurality of control parameters. The user input facility communicatively is configured to be initially associated with a first control parameter included in the plurality of control parameters in order to facilitate manual adjustment of the first control parameter. The user input facility is further configured to be selectively disassociated with the first control parameter and associated with a second control parameter included in the plurality of control parameters in order to facilitate manual adjustment of the second control parameter.

Another exemplary cochlear implant system includes a sound processing unit configured to apply noise reduction to an audio signal in accordance with a noise reduction parameter, an implantable cochlear stimulator communicatively coupled to the sound processing unit and configured to apply stimulation representative of the noise reduced audio signal to a patient via one or more electrodes, and a user input facility communicatively coupled to the sound processing unit and configured to facilitate manual adjustment of the noise reduction parameter.

An exemplary method includes 1) processing an audio signal in accordance with a plurality of control parameters, 2) directing an implantable cochlear stimulator to apply electrical stimulation representative of the audio signal to a patient via one or more electrodes, 3) initially associating a user input facility with a first control parameter included in the plurality of control parameters in order to facilitate manual adjustment of the first control parameter, and 4) selectively disassociating the user input facility with the first control parameter and associating the user input facility with a second control parameter in order to facilitate manual adjustment of the second control parameter.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for facilitating manual adjustment of one or more control parameters governing an operation of a cochlear implant system are described herein. In some examples, a cochlear implant system may include a sound processing unit configured to process an audio signal and an implantable cochlear stimulator communicatively coupled to the sound processing unit and configured to apply stimulation representative of the audio signal to a patient via one or more electrodes. The sound processing unit and the implantable cochlear stimulator are configured to operate in accordance with a plurality of control parameters. Exemplary control parameters include, but are not limited to, volume control parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and back-end dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters.

In some examples, a user input facility is communicatively coupled to at least one of the sound processing unit and the implantable cochlear stimulator. The user input facility is configured to be selectively associated with one or more of the control parameters to facilitate manual adjustment of the one or more of the control parameters. A patient may use the user input facility to transmit to the sound processing unit and/or implantable cochlear stimulator one or more commands configured to adjust a desired control parameter.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
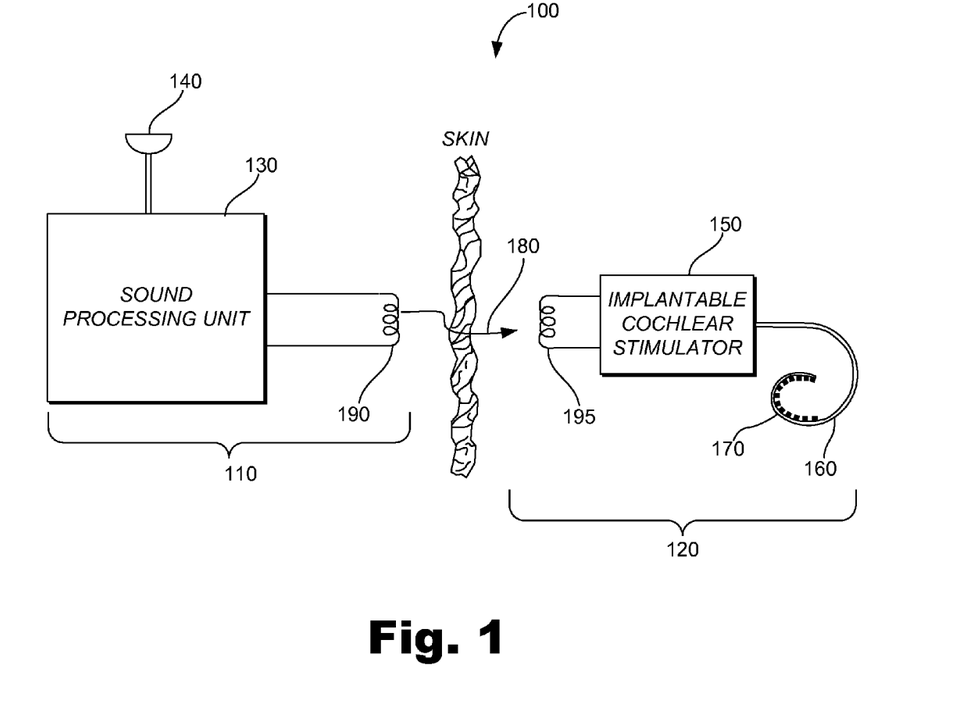
FIG. 1 illustrates an exemplary cochlear implant system according to principles described herein.

To facilitate an understanding of the methods and systems described herein, an exemplary cochlear implant system 100 will now be described in connection with FIG. 1. As shown in FIG. 1, the cochlear implant system 100, also referred to herein as a cochlear prosthesis, includes an external sound processor portion 110 and an implanted cochlear stimulation portion 120. The sound processor portion 110 may include a sound processing unit 130, a microphone 140, and/or additional circuitry as may serve a particular application. The cochlear stimulation portion 120 may include an implantable cochlear stimulator ("ICS") 150, a lead 160 with an array of electrodes 170 disposed thereon, and/or additional circuitry as may serve a particular application. It will be recognized that the sound processor portion 110 may alternatively be located internal to the patient.

The microphone 140 of FIG. 1 is configured to sense or detect audio signals and convert the sensed signals into corresponding electrical signals. In some examples, the audio signal may include speech. The audio signal may additionally or alternatively include music, noise, and/or other sounds. The electrical signals are sent to the sound processing unit 130 over an electrical or other suitable link. Alternatively, the microphone 140 may be connected directly to, or integrated with, the sound processing unit 130.

The sound processing unit 130 may include any combination of hardware, software, and/or firmware as may serve a particular application. For example, the sound processing unit 130 may include one or more processors, digital signal processors ("DSPs"), filters, programmable memory units, storage mediums, etc.

In some examples, the sound processing unit 130 may be configured to process the converted audio signals in accordance with a selected sound processing strategy to generate one or more control signals. These control signals are configured to direct the implantable cochlear stimulator 150 to generate one or more electrical stimulation pulses to be applied to one or more stimulation sites within a patient, as will be described in more detail below.

The sound processing unit 130 shown in FIG. 1 may include or be implemented within one or more devices configured to be worn or otherwise accessed by a patient. For example, the sound processing unit 130 may include or be implemented within a behind-the-ear ("BTE") sound processor configured to be positioned behind the ear. Alternatively, the sound processing unit 130 may include or be implemented within a portable speech processor ("PSP") device, a conventional hearing aid, or any other type of sound processing unit.

The electrode lead 160 shown in FIG. 1 is configured to be inserted within a duct of a cochlea. As shown in FIG. 1, the electrode lead 160 includes a plurality of electrodes 170, e.g., sixteen electrodes, spaced along its length. It will be understood, however, that any number of electrodes 170 may be disposed on the electrode lead 160.

Electronic circuitry within the implantable cochlear stimulator 150 is configured to generate and apply electrical stimulation to one or more stimulation sites within the cochlea via selected stimulation channels (i.e., pairs or groups of the individual electrodes 170) in accordance with one or more control signals generated by the sound processing unit 130. Hence, as will be described in more detail below, one or more electrode leads 160 with one or more electrodes 170 disposed thereon may be implanted within a patient such that the electrodes 170 are in communication with one or more stimulation sites within the patient. As used herein, the term "in communication with" refers to the electrodes 170 being adjacent to, in the general vicinity of, in close proximity to, directly next to, or directly on the stimulation site.

One or more components of cochlear implant system 100 may be implanted within a patient's body while one or more components of cochlear implant system 100 may be located external to the patient. For example, the implantable cochlear stimulator 150 and lead 160 may be implanted within the patient while the sound processing unit 130 and the microphone 140 are configured to be located outside the patient, e.g., behind the ear. Hence, the implantable cochlear stimulator 150 and the sound processing unit 130 may be transcutaneously coupled via a suitable data or communications link 180. The communications link 180 allows power and control signals to be sent from the sound processing unit 130 to the implantable cochlear stimulator 150. In some embodiments, data and status signals may also be sent from the implantable cochlear stimulator 150 to the sound processing unit 130.

The external and implantable portions of the cochlear implant system 100 may each include one or more coils configured to transmit and receive power and/or control signals via the data link 180. For example, the external portion 110 of the cochlear implant system 100 may include an external coil 190 and the implantable portion of the cochlear implant system 120 may include an implantable coil 195. The external coil 190 and the implantable coil 195 may be inductively coupled to each other, thereby allowing data and power signals to be wirelessly transmitted between the external portion and the implantable portion of the cochlear implant system 100.

Figure 2:
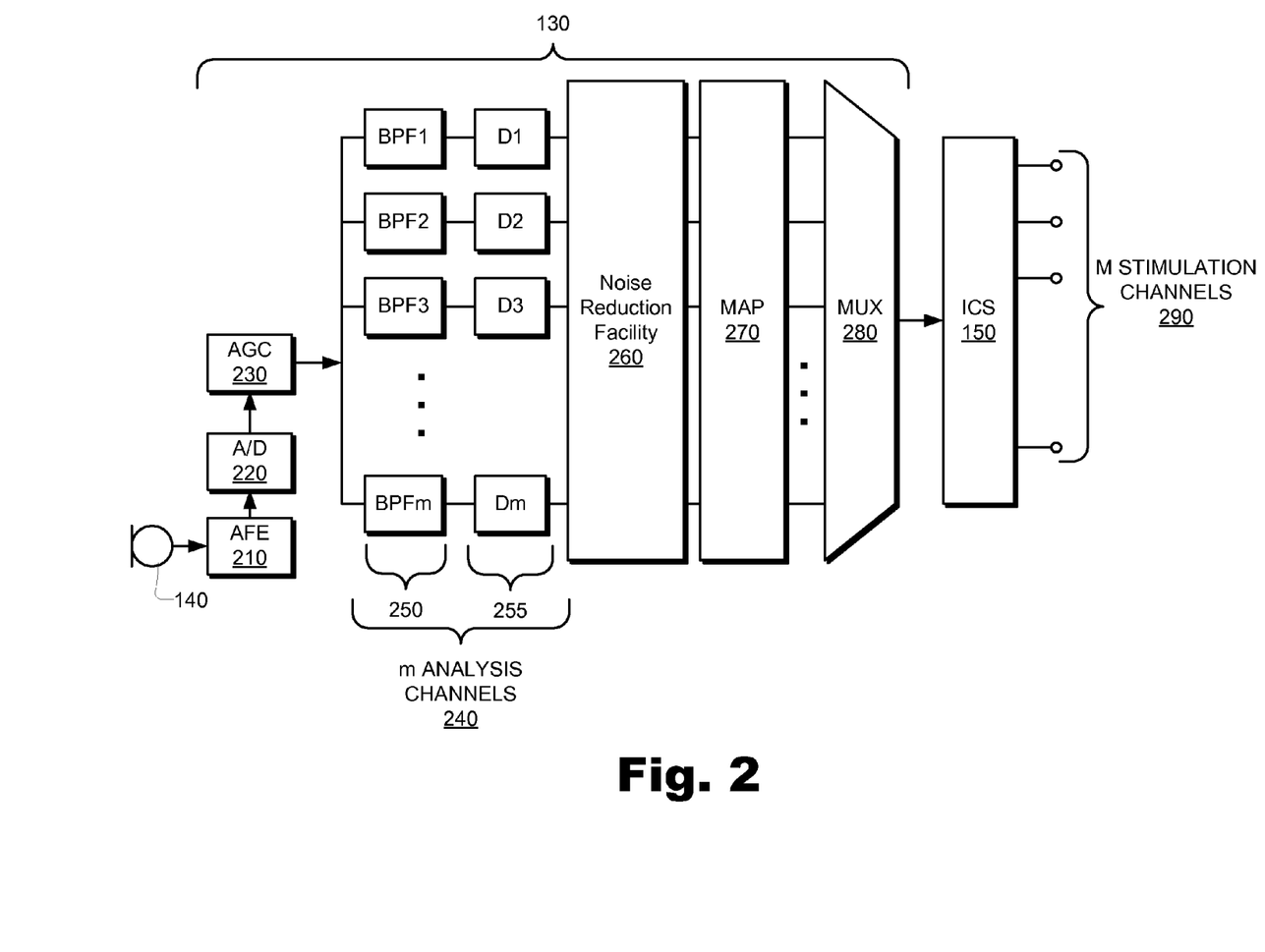
FIG. 2 is a functional block diagram of an exemplary sound processing unit and implantable cochlear stimulator according to principles described herein.

FIG. 2 is a functional block diagram of an exemplary sound processing unit 130 and implantable cochlear stimulator 150. The functions shown in FIG. 2 are merely representative of the many different functions that may be performed by sound processing unit 130 and/or implantable cochlear stimulator 150. One or more of the functions may be performed in accordance with one or more of the control parameters described herein.

As shown in FIG. 2, the microphone 140 senses an audio signal, such as speech or music, and converts the audio signal into an electrical signal. The electrical signal is then amplified with audio front-end ("AFE") circuitry 210. The amplified signal is converted to a digital signal by an analog-to-digital ("A/D") converter 220. The resulting digital signal is subjected to automatic gain control using a suitable automatic gain control ("AGC") function 230.

After appropriate automatic gain control, the digital signal is then processed in one of a number of digital signal processing or analysis channels 240. For example, the sound processing unit 130 may include, but is not limited to, eight analysis channels 240. Each analysis channel 240 may respond to a different frequency band of the sensed audio signal due to a series of band pass filters 250.

As shown in FIG. 2, each of the m analysis channels 240 may also include an energy detection stage (D1-Dm) 255. Each energy detection stage 255 may include any combination of circuitry configured to detect the amount of energy contained within each of the m analysis channels 240. For example, each energy detection stage 260 may include a rectification circuit followed by an integrator circuit.

As shown in FIG. 2, the signals within each of the analysis channels 240 may be processed by a noise reduction facility 260. Noise reduction facility 260 may include any combination of hardware and software and may be configured to apply one or more noise reduction functions to one or more of the signals within the analysis channels 240. For example, noise reduction facility 260 may be configured to increase a signal-to-noise ratio within one or more of the analysis channels 240. Noise reduction facility 260 will be described in more detail below.

Mapping stage 270 may be configured to map the signals in each of the m analysis channels 240 to one or more of M stimulation channels 290. In other words, the information contained in the m analysis channels 240 is used to define the electrical stimulation pulses that are applied to the patient by the implantable cochlear stimulator 150 via the M stimulation channels 290. As mentioned previously, pairs or groups of individual electrodes 170 may make up the M stimulation channels 290.

In some examples, the mapped signals are serialized by a multiplexer 280 and transmitted to the implantable cochlear stimulator 150. The implantable cochlear stimulator 150 may then apply electrical stimulation via one or more of the M stimulation channels 290 to one or more stimulation sites within the duct of the patient's cochlea. As used herein, the term "stimulation site" will be used to refer to a target area or location to which the electrical stimulation is applied. For example, a stimulation site may refer to any location within a region of auditory nerve tissue.

Figure 3:
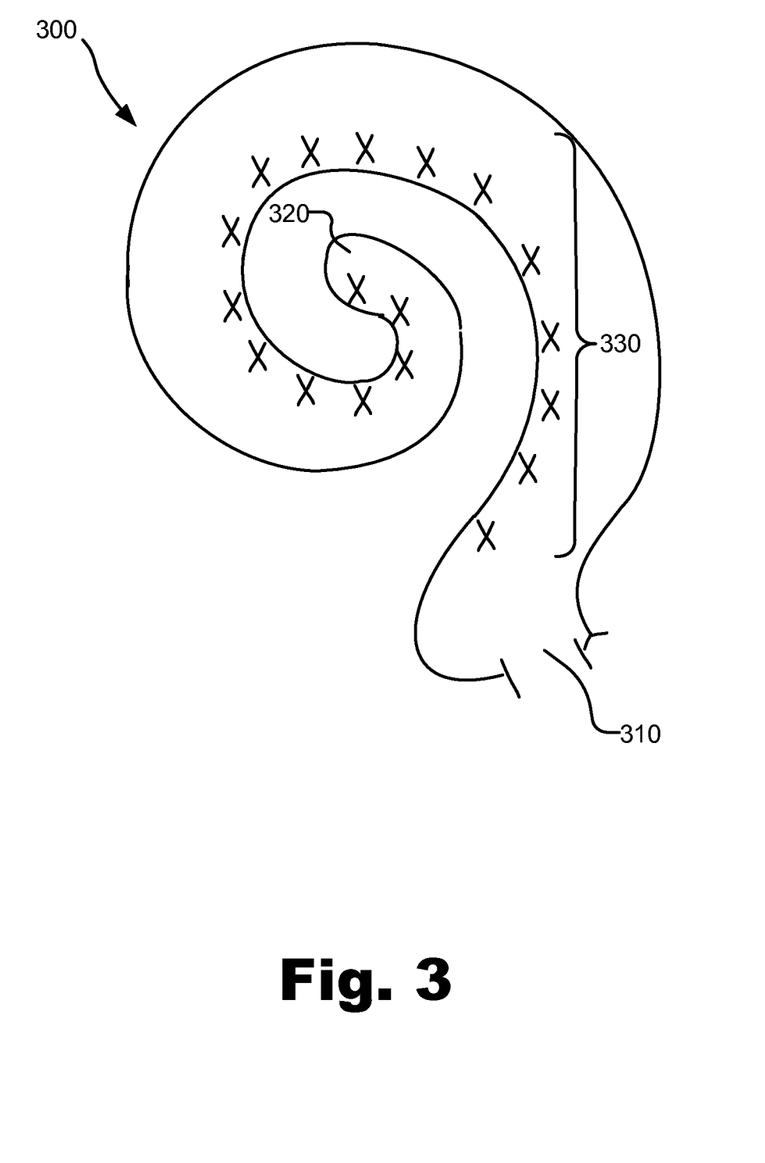
FIG. 3 illustrates a schematic structure of the human cochlea highlighting elements according to principles described herein.

FIG. 3 illustrates a schematic structure of the human cochlea 300. As shown in FIG. 3, the cochlea 300 is in the shape of a spiral beginning at a base 310 and ending at an apex 320. Within the cochlea 300 resides auditory nerve tissue 330, which is denoted by Xs in FIG. 3. The auditory nerve tissue 330 is organized within the cochlea 300 in a tonotopic manner. Low frequencies are encoded at the apex 320 of the cochlea 300 while high frequencies are encoded at the base 310. Hence, each location along the length of the cochlea 300 corresponds to a different perceived frequency. A cochlear prosthesis may therefore be implanted within a patient with sensorineural hearing loss and configured to apply electrical stimulation to different locations within the cochlea 300 to provide the sensation of hearing. For example, the electrode lead 114 may be disposed within the cochlea 300 such that the electrodes 170 are in communication with auditory nerve tissue 330 within the cochlea 300. Electrical stimulation may be applied by the electrodes 170 to the auditory nerve tissue 330.

The sound processing unit 130 and the implantable cochlear stimulator 150 may be configured to operate in accordance with one or more control parameters. These control parameters may include one or more stimulation parameters governing the electrical stimulation generated by the implantable cochlear stimulator 150, operating parameters, and/or any other parameter as may serve a particular application. As mentioned, exemplary control parameters include, but are not limited to, volume control parameters, noise reduction parameters, microphone sensitivity parameters, microphone direction parameters, pitch parameters, timbre parameters, sound quality parameters, most comfortable current levels ("M levels"), threshold current levels, channel acoustic gain parameters, front and backend dynamic range parameters, current steering parameters, pulse rate values, pulse width values, frequency parameters, amplitude parameters, waveform parameters, electrode polarity parameters (i.e., anode-cathode assignment), location parameters (i.e., which electrode pair or electrode group receives the stimulation current), stimulation type parameters (i.e., monopolar, bipolar, or tripolar stimulation), burst pattern parameters (e.g., burst on time and burst off time), duty cycle parameters, spectral tilt parameters, filter parameters, and dynamic compression parameters. Many other control parameters may be specified as may serve a particular application.

In some examples, it is desirable to facilitate manual adjustment of one or more control parameters governing the operation of the sound processing unit 130 and/or the implantable cochlear stimulator 150. In this manner, one or more control parameters may be adjusted by a user (e.g., the cochlear implant patient) to levels suitable for a particular patient. To this end, a user input facility may be provided and configured to be selectively associated with one or more control parameters in order to facilitate manual adjustment of the one or more control parameters. As will be described in more detail below, the user input facility may be communicatively coupled to at least one of the sound processing unit 130 and the implantable cochlear stimulator 150.

Figure 4:
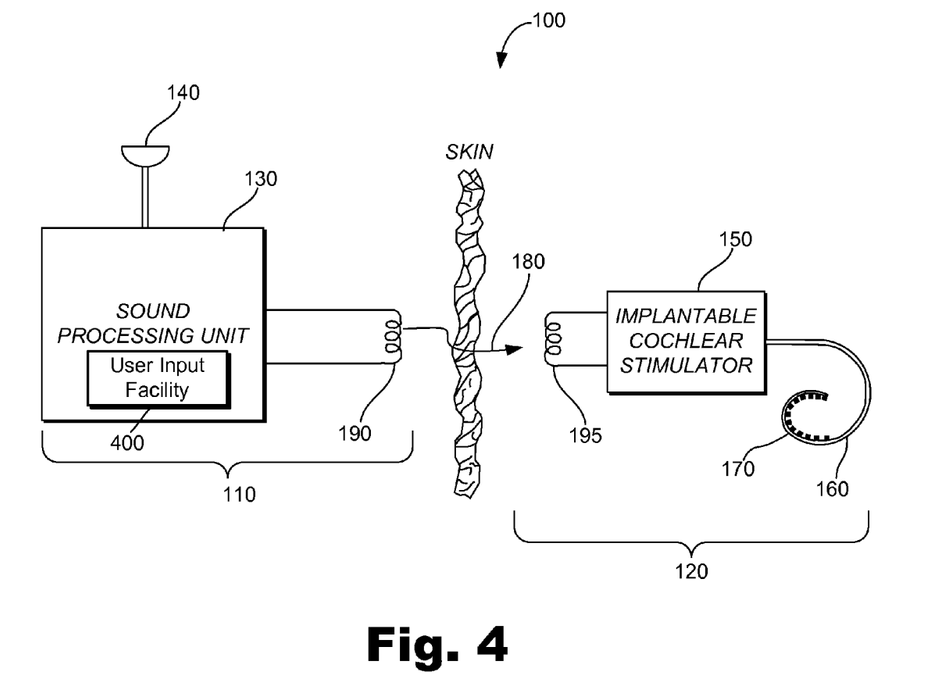
FIG. 4 illustrates an exemplary configuration of the cochlear implant system of FIG. 1 according to principles described herein.

FIG. 4 illustrates an exemplary configuration of cochlear implant system 100 wherein sound processing unit 130 includes a user input facility 400 configured to facilitate manual adjustment of one or more control parameters. User input facility 400 may include any combination of hardware and software. For example, the user input facility 400 may include a control dial or knob, one or more input keys, a graphical user interface, and/or any other mechanism, software application, or device as may serve a particular application.

User input facility 400 shown in FIG. 4 may be communicatively coupled to one or more components of sound processing unit 130 in order to facilitate manual adjustment of one or more control parameters governing the operation of sound processing unit 130 and/or implantable cochlear stimulator 150. For example, as will be described in more detail below, user input facility 400 may be communicatively coupled to noise reduction facility 260 in order to facilitate manual adjustment of one or more noise reduction parameters associated with an audio signal. It will be recognized that user input facility 400 may be additionally or alternatively coupled to any other component within sound processing unit 130 and/or implantable cochlear stimulator 150 as may serve a particular application.

Figure 5:
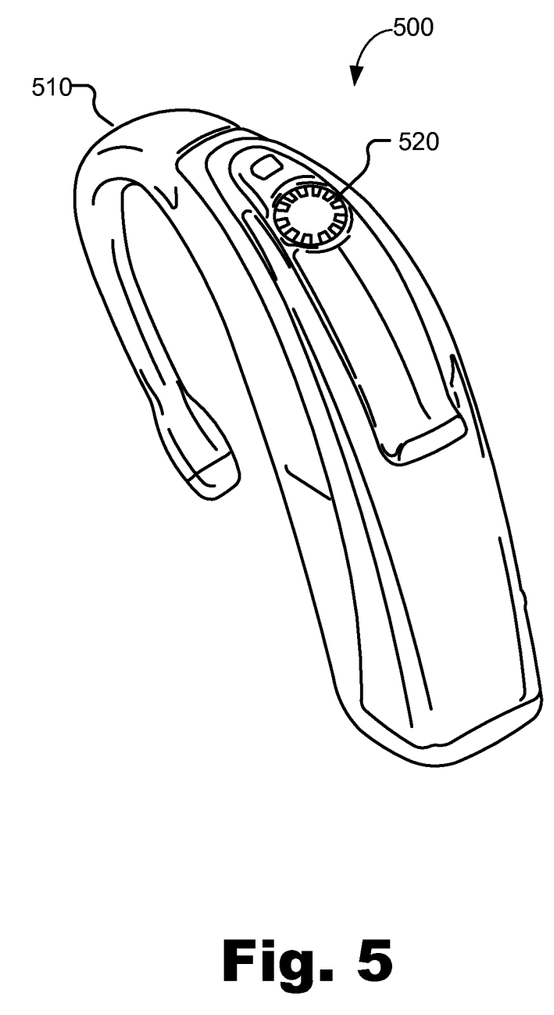
FIG. 5 shows an exemplary implementation of the cochlear implant system of FIG. 4 according to principles described herein.

FIG. 5 shows an exemplary implementation 500 of the cochlear implant system 100 of FIG. 4 wherein sound processing unit 130 includes a BTE sound processor 510. As shown in FIG. 5, the user input facility 400 may be implemented as a control dial 520 disposed at least partially on an outer surface of the BTE sound processor 510. The control dial 520 may be rotated or otherwise adjusted by a patient or other use to adjust one or more control parameters associated with the BTE sound processor 510 and/or the implantable cochlear stimulator 150. For example, the control dial 520 may be rotated in a clockwise direction to increase a volume level associated with an audio signal, increase an amount of noise reduction applied to an audio signal, and/or adjust any other control parameter as may serve a particular application. Likewise, the control dial 520 may be rotated in a counter-clockwise direction to decrease a volume level associated with an audio signal, decrease an amount of noise reduction applied to an audio signal, and/or adjust any other control parameter as may serve a particular application.

While a control dial 520 is shown in FIG. 5, it will be recognized that user input facility 400 may be alternatively implemented within BTE sound processor 510 in any other manner as may serve a particular application. For example, user input facility 400 may include one or more selectable buttons disposed on an outer surface of the BTE sound processor 510, one or more levers, and/or any other user input mechanism as may serve a particular application.

Figure 6:
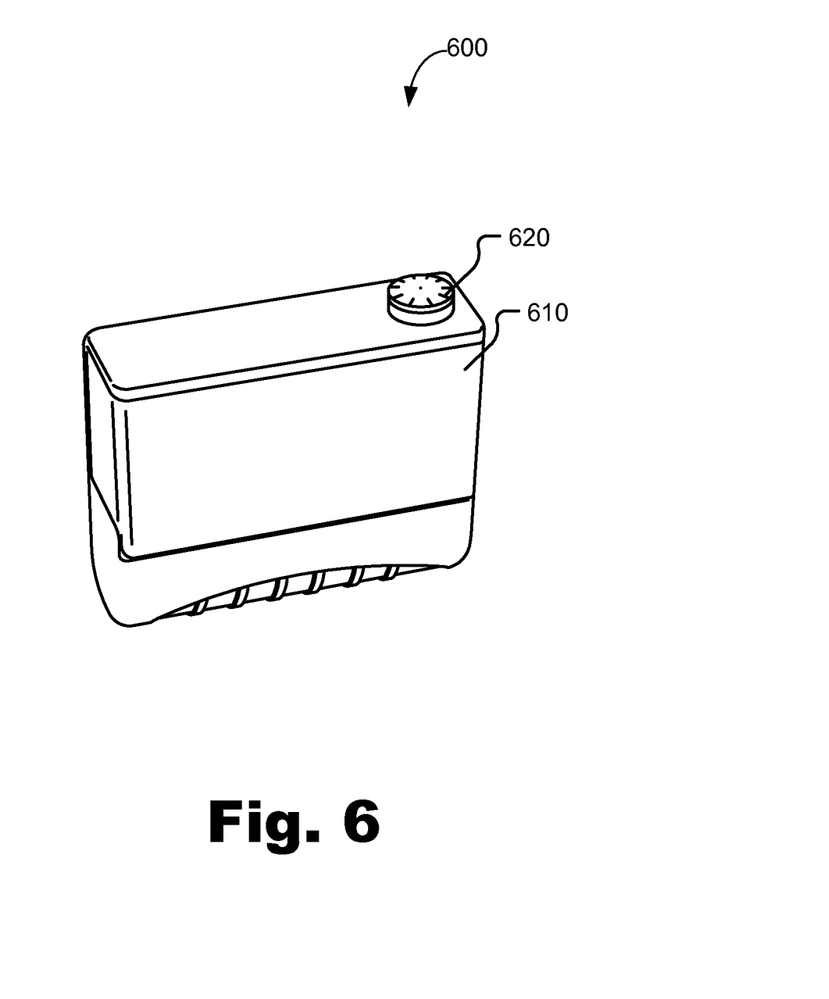
FIG. 6 illustrates an alternative implementation of the cochlear implant system of FIG. 4 according to principles described herein.

FIG. 6 illustrates an alternative implementation 600 of the cochlear implant system 100 of FIG. 4 wherein the sound processing unit 130 includes a PSP 610. As shown in FIG. 6, the user input facility 400 may be implemented as a control dial 620 disposed at least partially on an outer surface of the PSP 610. The control dial 620 may be rotated or otherwise adjusted by a patient or other user to adjust one or more control parameters associated with the PSP 610 and/or the implantable cochlear stimulator 150. For example, the control dial 620 may be rotated in a clockwise direction to increase a volume level associated with an audio signal, increase an amount of noise reduction applied to an audio signal, and/or adjust any other control parameter as may serve a particular application. Likewise, the control dial 620 may be rotated in a counter-clockwise direction to decrease a volume level associated with an audio signal, decrease an amount of noise reduction applied to an audio signal, and/or adjust any other control parameter as may serve a particular application.

Figure 7:
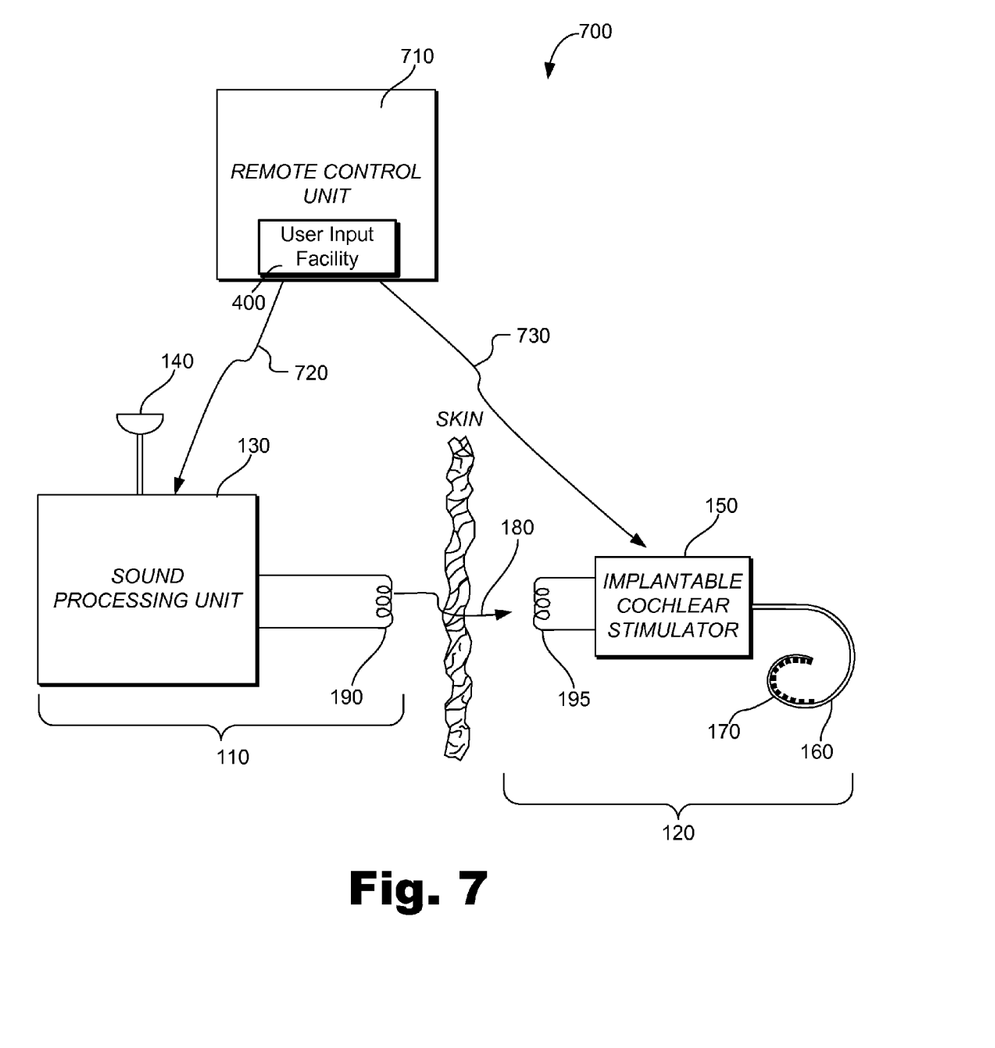
FIG. 7 illustrates an alternative cochlear implant system according to principles described herein.

FIG. 7 illustrates an alternative cochlear implant system 700 that may be used in accordance with the systems and methods described herein. As shown in FIG. 7, a remote control unit 710 may be communicatively coupled to sound processing unit 130 and/or implantable cochlear stimulator 150 via one or more communication links (e.g., communication links 720 and/or 730). Communication links 720 and 730 may include any type of communication link as may serve a particular application. For example, communication links 720 and/or 730 may each include, but are not limited to, a wireless communication link, an infrared link, a radio frequency ("RF") communication link, and/or any other type of communication link as may serve a particular application.

Remote control unit 710 may include any type of device configured to control the operation of sound processing unit 130 and/or implantable cochlear stimulator 150. For example, remote control unit 710 may include a handheld device, a personal computer, a personal digital assistant ("FDA"), a mobile phone, and/or any other device or apparatus as may serve a particular application. Remote control unit 710 may include any suitable combination of hardware and software configured to perform the functions described herein.

As shown in FIG. 7, user input facility 400 may be included within remote control unit 710 in order to facilitate manual adjustment of one or more control parameters with remote control unit 710. The user input facility 400 may include a control dial, one or more buttons, and/or any other user input facility as may serve a particular application.

While various implementations of user input facility 400 have been given herein, it will be recognized that each of the implementations is merely illustrative of the many different implementations of user input facility 400 that may be used in accordance with the systems and methods described herein. For example, in some implementations, user input facility 400 may include multiple user input facilities 400 each configured to facilitate adjustment of a distinct control parameter. To illustrate, the BTE sound processor 510 and/or the PSP 610 described herein may each include two or more user input facilities 400 each configured to facilitate adjustment of a distinct control parameter.

In some examples, user input facility 400 is configured to be selectively associated with one or more control parameters. In other words, user input facility 400 may be initially associated with a particular control parameter and then subsequently associated with another control parameter. In this manner, a patient may utilize the same user input facility 400 to adjust more than one control parameter. For example, the user input facility 400 may be initially associated with a first control parameter (e.g., a volume level associated with an audio signal), thereby allowing a patient to manually adjust the first control parameter. The user input facility 400 may then be selectively disassociated with the first control parameter and associated with a second control parameter (e.g., a noise reduction parameter associated with the audio signal), thereby allowing the patient to manually adjust the second control parameter. In some examples, sound processing unit 130 and/or remote control unit 710 may be configured to perform the selective association of one or more control parameters with user input facility 400.

For example, sound processing unit 130 may be configured to associate a control parameter with user input facility 400 in accordance with a particular "program" in which the sound processing unit 130 is configured to operate. In this manner, when sound processing unit 130 switches to a different program, the control parameter associated with the user input facility 400 may be changed or otherwise updated. Sound processing unit 130 may be configured to operate within any number of programs. Exemplary programs include, but are not limited to, a "normal" program wherein the sound processing unit 130 is configured to operate in accordance with one or more default control parameters, a "noise reduction" program wherein the sound processing unit 130 is configured to operate in accordance with one or more noise reduction parameters, and/or any other mode of operation as may serve a particular application.

Figure 8:
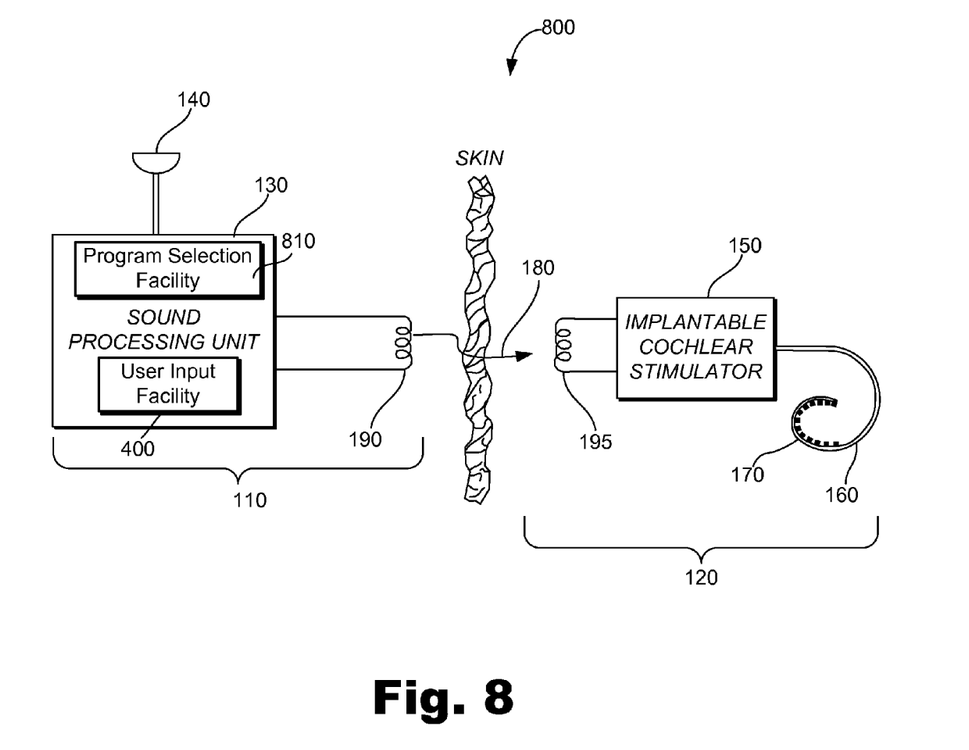
FIG. 8 shows an exemplary implementation of the cochlear implant system of FIG. 1 wherein the sound processing unit includes a program selection facility according to principles described herein.

In some examples, a patient may manually switch between different operating programs of the sound processing unit 130. For example, FIG. 8 shows an exemplary implementation 800 of cochlear implant system 100 wherein sound processing unit 130 includes a program selection facility 810. Program selection facility 810 may include any combination of hardware and software and may be configured to facilitate manual and/or automatic selection of one or more programs in which sound processing unit 130 may operate. To this end, program selection facility 810 may be communicatively coupled to processing circuitry within sound processing unit 130 and configured to direct the processing circuitry to switch from operating in accordance with a particular program to operating in accordance with another program (e.g., process an audio signal in accordance with the other program). While program selection facility 810 is shown to be included within sound processing unit 130, it will be recognized that program selection facility 810 may additionally or alternatively be included within remote control unit 710 or any other device as may serve a particular application.

Figure 9:
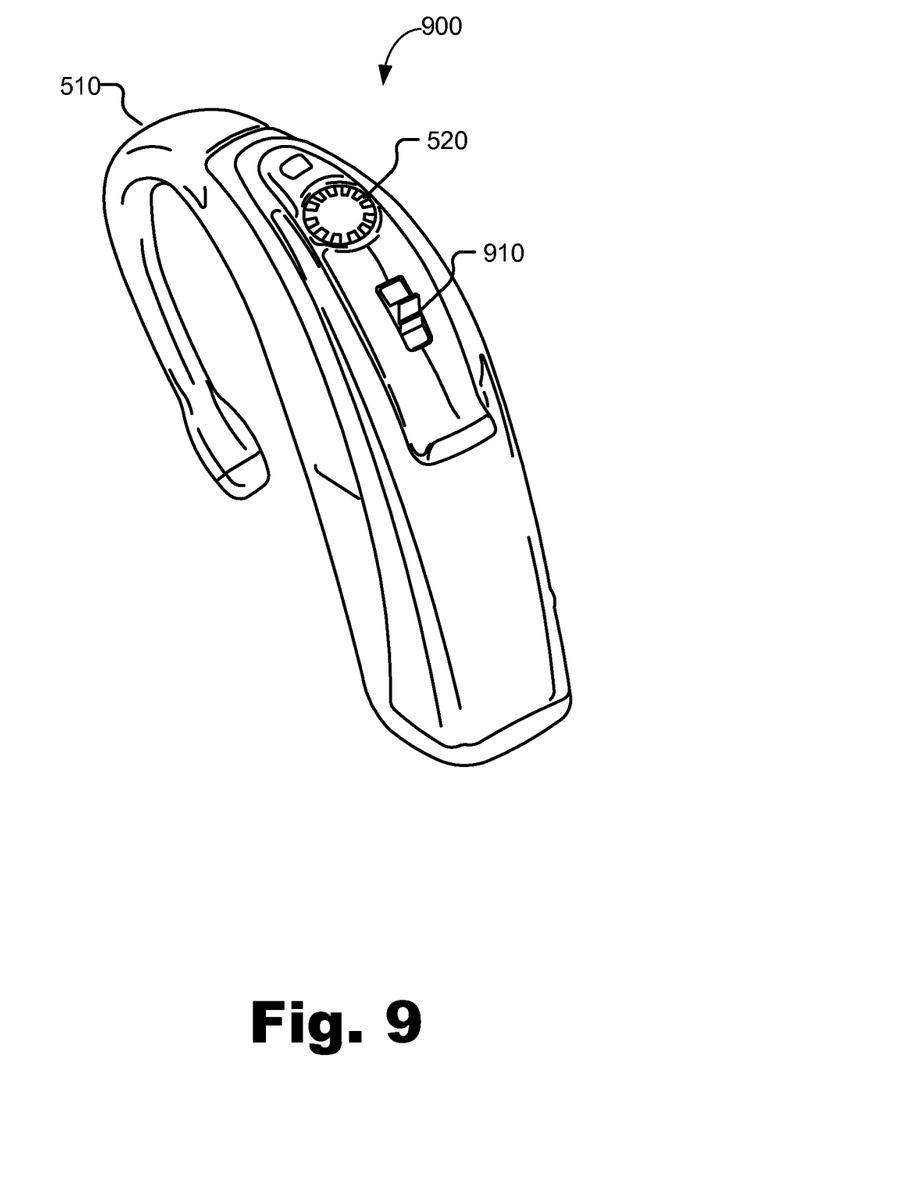
FIG. 9 illustrates an exemplary implementation of the cochlear implant system of FIG. 8 wherein the program selection facility includes a program switch at least partially disposed on an outer surface of a behind-the-ear sound processor according to principles described herein.

FIG. 9 illustrates an exemplary implementation 900 of cochlear implant system 800 wherein program selection facility 810 includes a program switch 910 at least partially disposed on an outer surface of BTE sound processor 510. Program switch 910 may be accessed by a patient and used to switch between different operating programs. For example, program switch 910 may be configured to be selectively positioned at one of two positions. Each position corresponds to a particular program. For example, a first position may correspond to a "normal" program wherein the sound processing unit 130 is configured to operate in accordance with one or more default control parameters. A second position may correspond to a "noise reduction" program, wherein sound processing unit 130 may be configured to operate in accordance with one or more noise reduction parameters.

In some alternative examples, sound processing unit 130 may be configured to automatically switch between operating programs and thereby automatically change the particular control parameter that is associated with user input facility 400. For example, sound processing unit 130 may be configured to switch between operating programs in response to a sensed listening environment or other factor. To illustrate, sound processing unit 130 may be configured to detect when the user enters a noisy environment and automatically switch to a "noise reduction" program so that a patient may utilize user input facility 400 to manually adjust one or more noise reduction parameters corresponding to an audio signal. It will be recognized that sound processing unit 130 may be configured to automatically switch to any other operating program as may serve a particular application.

As mentioned, a control parameter may be selectively associated with user input facility 400 in accordance with a particular program in which sound processing unit 130 is configured to operate. For example, a volume control parameter may be associated with user input facility 400 when sound processing unit 130 is configured to operate in accordance with a "normal" program. In this manner, a patient may utilize the user input facility 400 to manually adjust a volume level associated with an audio signal while the sound processing unit 130 is operating within the "normal" program. When the sound processing unit 130 switches to another program, the control parameter associated with the user input facility 400 may correspondingly change. For example, if the sound processing unit 130 switches to a "noise reduction" program, a noise reduction parameter may be selectively associated with the user input facility 400 so that the user may manually adjust a noise reduction level associated with the audio signal. It will be recognized that any other control parameter may be selectively associated with user input facility 400 as may serve a particular application.

Figure 10:
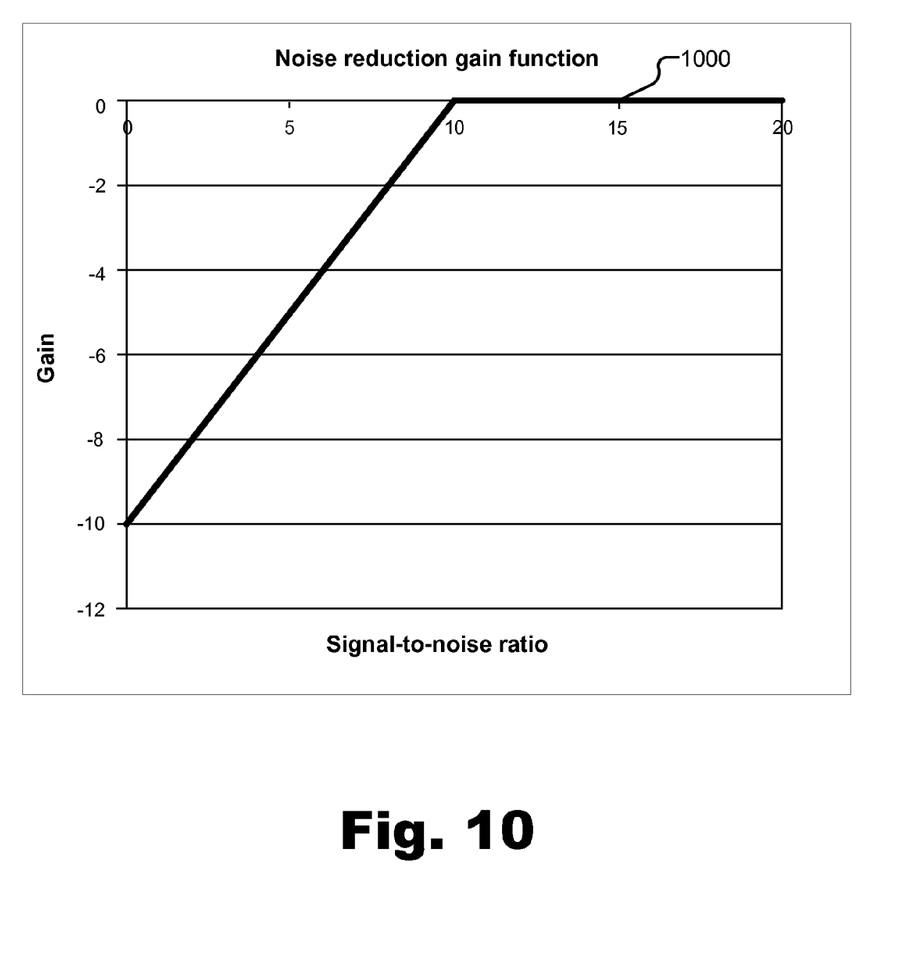
FIG. 10 illustrates an exemplary noise reduction gain function that may be used by a noise reduction facility to increase a signal-to-noise ratio within one or more of analysis channels according to principles described herein.

An example of how user input facility 400 may be used to manually adjust one or more noise reduction parameters associated with an audio signal will now be given in connection with FIG. 10. As mentioned, sound processing unit 130 may include a noise reduction facility 260 configured to increase a signal-to-noise ratio within one or more analysis channels 240. Noise reduction facility 260 may be configured to operate in accordance with a noise reduction gain function. FIG. 10 illustrates an exemplary noise reduction gain function 1000 that may be used by noise reduction facility 260 to increase a signal-to-noise ratio within one or more of the analysis channels 240.

As shown in FIG. 10, noise reduction facility 260 may be configured to apply gain to each of the analysis channels 240 depending on the signal-to-noise ratios in each of the analysis channels 240. For example, if a signal-to-noise ratio within a particular analysis channel 240 is equal to zero, noise reduction facility 260 may be configured to apply −10 dB gain to that channel. However if the signal-to-noise ratio within a particular analysis channel 240 is already equal to or greater than 10, noise reduction facility 260 does not apply any gain to that channel. By applying a negative amount of gain within a particular analysis channel 240, the signal-to-noise ratio within the channel may be increased.

Hence, by adjusting user input facility 400, a user may manually adjust the amount of gain or noise reduction that is applied to one or more of the analysis channels 240. For example, if a user desires to increase the amount of noise reduction that is applied to a particular audio signal, the user may adjust user input facility 400 accordingly (e.g., rotate control dial 520 in a clockwise direction). Likewise, if the patient desires to decrease the amount of noise reduction that is applied to a particular audio signal, the user may adjust the user input facility 400 accordingly (e.g., rotate control dial 520 in a counter-clockwise direction). In response to a detected interaction of the user with user input facility 400, sound processing unit 130 may adjust a noise parameter (e.g., an amount of gain or noise reduction applied to one or more analysis channels 240) accordingly.

While the examples given herein have illustrated how a volume control parameter and/or one or more noise reduction parameters may be selectively associated with user input facility 400, it will be recognized that any of the other control parameters described herein may be additionally or alternatively associated with user input facility 400. For example, a patient may desire to manually adjust a sensitivity of microphone 140. In this instance, the patient may direct sound processing unit 130 to selectively associate a microphone sensitivity parameter with user input facility 400 (e.g., by selecting a predefined program with program selection facility 840 or in any other suitable manner). Once the association is established, adjustment of user input facility 400 may result in an adjustment of the sensitivity of the microphone 140.

Another exemplary control parameter that may be associated with user input facility 400 to facilitate manual adjustment thereof is a "stimulation type" control parameter. By adjusting the stimulation type, the patient may direct implantable cochlear stimulator 150 to apply different types of stimulation to one or more stimulation sites within the cochlea. For example, the implantable cochlear stimulator 150 may be selectively directed to apply monopolar, bipolar, or tripolar stimulation to one or more stimulation sites within the cochlea. User input facility 400 may additionally or alternatively be used to adjust an amount of compensation current applied to one or more electrodes 170 designated as compensating electrodes during bipolar and/or tripolar stimulation.

Figure 11:
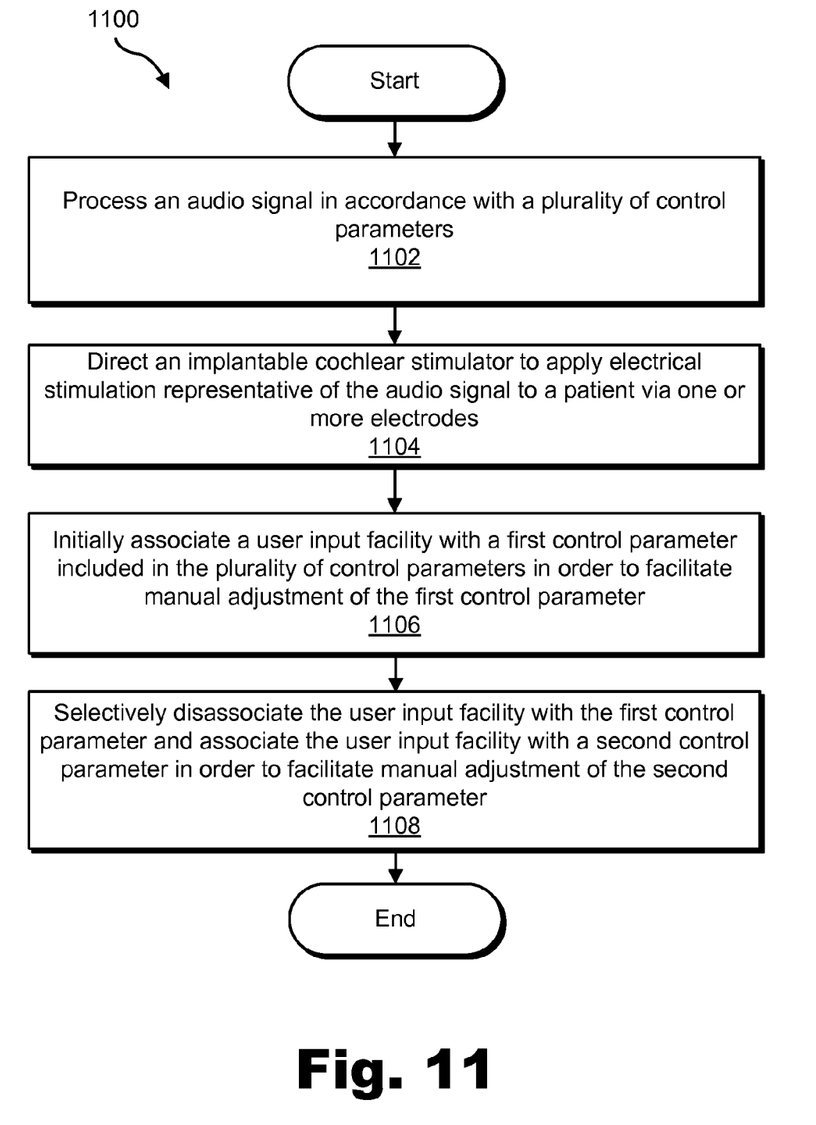
FIG. 11 illustrates an exemplary method of facilitating manual adjustment of one or more cochlear implant system control parameters according to principles described herein.

FIG. 11 illustrates an exemplary method of facilitating manual adjustment of one or more control parameters governing an operation of a sound processing unit (e.g., sound processing unit 130) and/or an implantable cochlear stimulator (e.g., implantable cochlear stimulator 150). While FIG. 11 illustrates exemplary steps according to one embodiment, other embodiments may omit, add to, reorder, and/or modify any of the steps shown in FIG. 11. It will be recognized that any of the components described herein may perform one or more of the steps shown in FIG. 11. For example, one or more of the steps shown in FIG. 11 may be performed by sound processing unit 130.

In step 1102, an audio signal is processed in accordance with a plurality of control parameters. The audio signal may be processed in any of the ways described herein. The plurality of control parameters may include any of the control parameters described herein.

In step 1104, an implantable cochlear stimulator is directed to apply electrical stimulation representative of the audio signal to a patient via one or more electrodes. The implantable cochlear stimulator may be directed to apply the electrical stimulation in any of the ways described herein.

In step 1106, a user input facility may be initially associated with a first control parameter included in the plurality of control parameters in order to facilitate manual adjustment of the first control parameter. The association may be performed by sound processing unit 130 in any of the ways described herein. Alternatively, the association may be performed by remote control unit 710.

In step 1108, the user input facility is selectively disassociated with the first control parameter and associated with a second control parameter in order to facilitate manual adjustment of the second control parameter. The disassociation and association may be performed by sound processing unit 130 and/or remote control unit 710 in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sound processing unit that operates in accordance with a first program by applying noise reduction to an audio signal in accordance with a noise reduction parameter while the sound processing unit operates in accordance with the first program;
an implantable cochlear stimulator communicatively coupled to the sound processing unit and that applies stimulation representative of the noise reduced audio signal to a patient via one or more electrodes while the sound processing unit operates in accordance with the first program; and
a user input facility communicatively coupled to the sound processing unit and that is associated with the noise reduction parameter while the sound processing unit operates in accordance with the first program in order to facilitate manual adjustment of the noise reduction parameter while the sound processing unit operates in accordance with the first program;
wherein the sound processing unit switches from operating in accordance with the first program to operating in accordance with a second program by processing the audio signal in accordance with an additional control parameter other than the noise reduction parameter, and
wherein, in response to the sound processing switching from operating in accordance with the first program to operating in accordance with the second program, the user input facility is disassociated from the noise reduction parameter and associated with the additional control parameter in order to facilitate manual adjustment of the additional control parameter while the sound processing unit operates in accordance with the second program.

2. The system of claim 1, wherein the user input facility is at least partially disposed on an outer surface of the sound processing unit.

3. The system of claim 1, wherein the user input facility is a part of a remote control unit communicatively coupled to the sound processing unit.

4. The system of claim 1, wherein the user input facility comprises a control dial.

5. The system of claim 1, wherein the additional control parameter comprises a volume parameter associated with the audio signal, a microphone direction parameter, a microphone sensitivity parameter, a compensation current parameter, a stimulation type parameter, a pitch parameter, a timbre parameter, a sound quality parameter, a most comfortable current level, a threshold current level, a channel acoustic gain parameter, a dynamic range parameter, a current steering parameters, a pulse rate value, a pulse width value, a frequency parameter, an amplitude parameter, a waveform parameter, an electrode polarity parameter, a location parameter, a burst pattern parameter, a duty cycle parameter, a spectral tilt parameter, a filter parameter, or a dynamic compression parameter.

6. The system of claim 1, wherein the noise reduction parameter does not include a volume parameter associated with the audio signal.

7. The system of claim 1, further comprising a program switch communicatively coupled to the sound processing unit and that directs the sound processing unit to switch from operating in accordance with the first program to operating in accordance with the second program.

8. The system of claim 7, wherein the program switch senses a listening environment of the patient and automatically directs the sound processing unit to switch from operating in accordance with the first program to operating in accordance with the second program in accordance with the sensed listening environment.

9. The system of claim 7, wherein the program switch directs the sound processing unit to switch from operating in accordance with the first program to operating in accordance with the second program in response to interaction of a user with the program switch.

10. The system of claim 1, wherein the sound processing unit adjusts an amount of the noise reduction in response to interaction of a user with the user input facility while the sound processing unit operates in accordance with the first program.

11. The system of claim 1, wherein the sound processing unit does not process the audio signal in accordance with the noise reduction parameter while the sound processing unit operates in accordance with the second program.

12. The system of claim 1, wherein the implantable cochlear stimulator applies stimulation representative of the audio signal that has been processed in accordance with the additional control parameter to the patient via the one or more electrodes while the sound processing unit operates in accordance with the second program.

13. The system of claim 1, wherein the sound processing unit adjusts a signal-to-noise ration of the audio signal in response to user interaction with the user input facility while the sound processing unit operates in accordance with the first program.

14. A method comprising:
operating, by a sound processing unit included in a cochlear implant system, in accordance with a first program by applying noise reduction to an audio signal in accordance with a noise reduction parameter while the sound processing unit operates in accordance with the first program;
adjusting, by the sound processing unit while the sound processing unit operates in accordance with the first program, an amount of the noise reduction applied to the audio signal in response to an interaction by a user with a user input facility that is associated with the noise reduction parameter while the sound processing unit operates in accordance with a first program;
switching, by the sound processing unit, from operating in accordance with the first program to operating in accordance with the second program by processing the audio signal in accordance with an additional control parameter other than the noise reduction parameter; and
selectively disassociating, by the sound processing unit in response to the sound processing unit switching from operating in accordance with the first program to operating in accordance with the second program, the user input facility with the noise reduction parameter and associating the user input facility with the additional control parameter.

15. The method of claim 14, further comprising:
processing, by the sound processing unit, the audio signal in accordance with the additional control parameter and not in accordance with the noise reduction parameter while the sound processing unit operates in accordance with the second program; and
adjusting, by the sound processing unit while the sound processing unit operates in accordance with the second program and in response to an interaction by the user with a user input facility, a manner in which the audio signal is processed in accordance with the additional control parameter.

16. The method of claim 14, further comprising directing, by the sound processing unit while the sound processing unit operates in accordance with the first program, an implantable cochlear stimulator to apply electrical stimulation representative of the noise reduced audio signal to a patient via one or more electrodes.

17. The method of claim 14, wherein the user input facility is at least partially disposed on an outer surface of the sound processing unit.

18. The method of claim 14, wherein the user input facility is a part of a remote control unit communicatively coupled to the sound processing unit.

19. The method of claim 14, wherein the user input facility comprises a control dial.

* * * * *